United States Patent
Hisatake et al.

(10) Patent No.: US 7,220,855 B2
(45) Date of Patent: May 22, 2007

(54) PROCESS FOR PRODUCING METHYLCOBALAMIN

(75) Inventors: Yoshihiko Hisatake, Ibaraki (JP); Takuo Tanaka, Ibaraki (JP); Tomio Tsurugi, Chiba (JP); Hiroshi Kuroda, Ibaraki (JP)

(73) Assignee: Eisai Co., Ltd., Tokyo (JP)

(*) Notice: Subject to any disclaimer, the term of this patent is extended or adjusted under 35 U.S.C. 154(b) by 0 days.

(21) Appl. No.: 10/476,381

(22) PCT Filed: Jun. 4, 2002

(86) PCT No.: PCT/JP02/05510

§ 371 (c)(1),
(2), (4) Date: Oct. 30, 2003

(87) PCT Pub. No.: WO02/098896

PCT Pub. Date: Dec. 12, 2002

(65) Prior Publication Data

US 2004/0132687 A1    Jul. 8, 2004

(30) Foreign Application Priority Data

Jun. 5, 2002  (JP) .................... 2001-169107

(51) Int. Cl.
*C07H 23/00* (2006.01)
(52) U.S. Cl. .................................. 536/26.41
(58) Field of Classification Search ............ 536/26.41, 536/17.1, 117; 540/452
See application file for complete search history.

(56) References Cited

U.S. PATENT DOCUMENTS 3,798,211 A   3/1974  Mervyn
3,928,320 A * 12/1975  Boige ................ 536/26.41
6,657,057 B2 * 12/2003  Hisatake et al. ......... 540/452

FOREIGN PATENT DOCUMENTS

| GB | 1355899 A | 6/1974 |
|---|---|---|
| JP | 45-38059 B1 | 12/1970 |
| JP | 49-47899 A2 | 5/1974 |
| JP | 50-41900 A2 | 4/1975 |
| JP | 50-38120 B4 | 12/1975 |
| WO | WO 01/42271 A1 | 6/2001 |

OTHER PUBLICATIONS

Amijee, M. et al., Journal of Chromatography A (1996), vol. 738, pp. 43 to 55.
Database CAPLUS on STN, AN 1987:210255, Matos, J. et al., abstract, Biotechnol. Appl. Biochem., 1987, vol. 9, No. 1, pp. 39 to 52.
Byrne, B. et al., Tetrahedron Letters, 1986, vol. 27, No. 11, pp. 1233 to 1236.
Rachkus et al., Papers of Lithuanian Academy of Sciences, Series V, vol. 1, No. 85, pp. 133-141, (1979).

* cited by examiner

*Primary Examiner*—Elli Peselev
(74) *Attorney, Agent, or Firm*—Birch, Stewart, Kolasch & Birch, LLP

(57) ABSTRACT

The present invention provides a novel industrially excellent and ecological process for producing methylcobalamin which is useful as a medicament etc. More specifically, it provides a process for producing methylcobalamin by reducing cyanocobalamin or hydroxocobalamin in the presence of a reducing agent, and then methylating the reductant by adding a water-soluble methylating agent.

7 Claims, No Drawings

PROCESS FOR PRODUCING METHYLCOBALAMIN

This application is the national phase under 35 U.S.C. §371 of PCT International Application No. PCT/JP02/05510 which has an International filing date of Jun. 4, 2002, which designated the United States of America.

TECHNICAL FIELD

The present invention relates to an industrially excellent process for producing methylcobalamin. Specifically, it also relates to a novel production method which is free from the formation of a malodorous harmful substance and is ecological, and to a process for inhibiting the formation of such a malodorous harmful substance in a production process of methylcobalamin (V).

PRIOR ART

Methylcobalamin is a coenzymatic vitamin B12 present in the blood and spinal fluid. It can more satisfactorily migrate into the nerve tissues than the other B12 homologues and is used for prophylaxis, therapy, and amelioration of diabetic neuropathy, multiple neuritis, and other peripheral neuropathy, especially of numbness, pain, and paralysis and for megaloblast anaemia caused by a deficiency of vitamin B12.

Methylcobalamin has been conventionally produced by the following preparation methods:
(1) a method of reacting hydroxocobalamin with a dicarboxylic acid monomethyl ester in the presence of a powdered metal (JP-A 49-47899);
(2) a method of reacting cyanocobalamin with monomethyl oxalate in hydrous methanol in the presence of a powdered metal (JP-A 50-41900);
(3) a method of reacting hydroxocobalamin with methylmercury iodide or ammonium methylhexafluorosilicate (JP-A 50-38120); and
(4) a method of reacting cyanocobalamin with methyl iodide in the presence of sodium borohydride (JP-A 45-38059).

However, dicarboxylic acid monomethyl esters such as monomethyl oxalate used in the methods (1) and (2) are not commercially available, must be prepared before use and cannot be used in commercial production. In addition, zinc powder used as the powdered metal is a heavy metal, it is indispensable to take measures for preventing its contamination into products and for protecting the environment, and it is not industrially desirable.

In the method (3), methylmercury iodide used is a pollutant and cannot be used industrially. In addition, ammonium methylhexafluorosilicate is not commercially available, must be prepared before use cannot be used industrially.

In contrast, the production method (4) is very excellent in view of yield and product purity. However, methyl iodide has a very low boiling point (41° C. to 43° C.) and is thereby difficult to handle. Accordingly, this method is not sufficient as an industrial method for commercial production. In addition, from the viewpoint of protecting working environment or natural environment, the use of methyl iodide assigned as a specified chemical substance and having toxicity such as potential carcinogenicity is by no means preferable in view of industrial health of factory workers. To obtain highly pure methylcobalamin by the method using methyl iodide, one or more purification procedures by column chromatography are generally necessary, thus inviting a serious problem in operation and production cost. In addition, the column purification requires a large amount of an organic solvent and an enormous quantity of a waste liquid.

Thus, an industrially excellent process for producing methylcobalamin has not yet been established and hence a novel excellent method has been desired.

Accordingly, an object of the present invention is to provide an industrially excellent process for producing methylcobalamin, especially a novel process for producing methylcobalamin, which process does not require methyl iodide and purification by column chromatography and is ecological. Another object of the present invention is to provide a novel production method which does not invite the formation of a malodorous harmful substance and is ecological, and a process for inhibiting the formation of a malodorous harmful substance in a production process of methylcobalamin (V).

DISCLOSURE OF INVENTION

The present invention provides, in an aspect, a process for producing methylcobalamin (V) which is represented by the following reaction formula including a reduction process and a methylation process.

Reduction process: Cobalamin-CN or Cobalamin-OH→Cobalamin

Methylation process: Cobalamin→Cobalamin-CH₃

Specifically, the present invention provides a process for producing methylcobalamin (V), comprising the steps of reducing cyanocobalamin (I) or hydroxocobalamin (II) represented by the following formula in the presence of a reducing agent (III), and then methylating the reductant by adding a water-soluble methylating agent (IV).

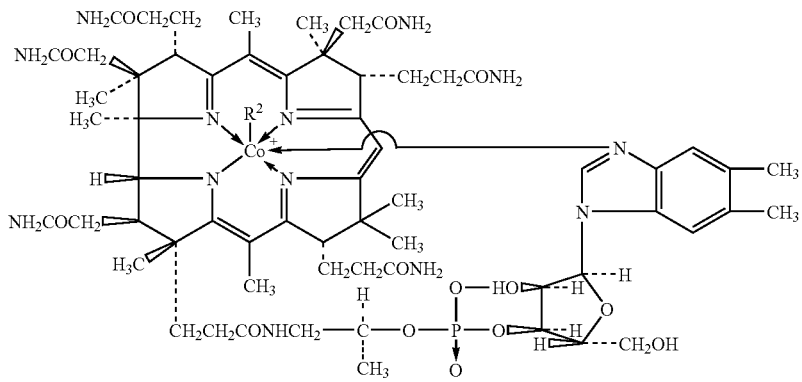

R²=CN: Cyanocobalamin (I)
R²=OH: Hydroxocobalamin (II)
R²=CH₃: Methylcobalamin (V)

In another aspect, the present invention provides a process for producing methylcobalamin (V), comprising the steps of reducing cyanocobalamin (I) or hydroxocobalamin (II) in an aqueous solution or a hydrous organic solvent in the presence of a reducing agent (III); and then methylating the reductant by adding a water-soluble methylating agent (IV).

The present invention further provides a process for producing methylcobalamin (V), comprising the steps of reducing cyanocobalamin (I) or hydroxocobalamin (II) in an aqueous solution or a hydrous organic solvent in the presence of a reducing agent (III); methylating the reductant by adding a water-soluble methylating agent (IV); and then precipitating the reaction product as crystals or precipitates.

The present invention provides, in yet another aspect, a process for producing methylcobalamin (V), comprising the steps of reducing cyanocobalamin (I) or hydroxocobalamin (II) in an aqueous solution or a hydrous organic solvent in the presence of a cyanide ion scavenger and a reducing agent (III); methylating the reductant by adding a water-soluble methylating agent; and then precipitating the reaction product as crystals or precipitates.

In addition, the present invention provides a process for inhibiting the formation of malodorous dimethyl sulfide in a production process of methylcobalamin (V) using a trimethylsulfur derivative (VI) as a methylating agent, which comprises the steps of reducing cyanocobalamin (I) or hydroxocobalamin (II) in the presence of a reducing agent (III); and then methylating the reductant by adding trimethylsulfoxonium iodide, trimethylsulfoxonium bromide and/or trimethylsulfoxonium chloride.

According to the present invention, the reducing agent and the water-soluble methylating agent are added separately at different timings to the reaction system. Specifically, in the reduction process, the reducing agent is added to the reaction system to thereby convert cyanocobalamin (I) or hydroxocobalamin (II) into a reductant. After the reduction process, the water-soluble methylating agent is added to the reaction system to thereby yield methylcobalamin. In the reduction process, whether cyanocobalamin (I) or hydroxocobalamin (II) is converted into a reductant can be generally verified by whether cyanocobalamin (I) or hydroxocobalamin (II) disappears in a separation analysis using, for example, high-performance liquid chromatography. The termination of hydrogen evolution by action of the reducing agent demonstrates the completion of the reduction process.

Cyanocobalamin (I), hydroxocobalamin (II) and methylcobalamin (V) relating to the present invention are known natural compounds.
Cyanocobalamin (CAS Registry Number: 68-19-9)
Hydroxocobalamin (CAS Registry Number: 13422-51-0)
Methylcobalamin (CAS Registry Number: 13422-55-4)

The water-soluble methylating agent (IV) for use in the present invention is not specifically limited, as long as it has a solubility in water at room temperature of 2% or more, and includes, for example, trimethylsulfur derivatives (VI) represented by the following formula. In the formula, X is a halogen atom or a methoxysulfonyloxy group; and n is 0 or 1.

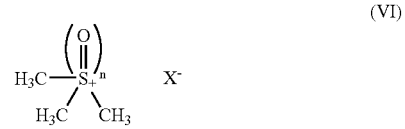

Examples of the trimethylsulfur derivatives (VI) include, but are not limited to, the following compounds.
(1) Trimethylsulfoxonium iodide (CAS Registry Number: 1774-47-6)
(2) Trimethylsulfonium iodide (CAS Registry Number: 2181-42-2)
(3) Trimethylsulfoxonium chloride (CAS Registry Number: 5034-06-0)
(4) Trimethylsulfonium chloride (CAS Registry Number: 3086-29-1)
(5) Trimethylsulfoxonium bromide (CAS Registry Number: 3084-53-5)
(6) Trimethylsulfonium bromide (CAS Registry Number: 25596-24-1)
(7) Trimethylsulfonium methylsulfate (CAS Registry Number: 2181-44-4)

All these compounds are known substances. Among them, trimethylsulfoxonium iodide, trimethylsulfonium iodide, trimethylsulfoxonium chloride, trimethylsulfoxonium bromide and trimethylsulfonium bromide are available at low cost as reagents or industrial starting materials. Trimethylsulfonium chloride can be easily obtained by synthesis according to the method described by B. Byrne et al. in Tetrahedron Lett., 27, 1233, (1986).

Among the trimethylsulfur derivatives (VI), trimethylsulfoxonium bromide, trimethylsulfonium bromide, trimethylsulfoxonium chloride and trimethylsulfonium chloride particularly exhibit a high solubility in water and have a characteristic that the use in a smaller amount yields highly pure methylcobalamin in a high yield.

The amount of the trimethylsulfur derivative (VI) is not specifically limited and is generally from 1.0 to 5 equivalents, preferably from 1.1 to 4.5 equivalents, and more preferably from 1.2 to 4 equivalents to cyanocobalamin (I) or hydroxocobalamin (II).

The reducing agent (III) for use in the present invention is not specifically limited, as long as it can be used in the synthesis of cyanocobalamin (I) or hydroxocobalamin (II), and includes, for example, sodium borohydride, lithium borohydride, NaBH₃CN (sodium cyanoborohydride), and Red-Al (sodium bis(2-methoxyethoxy)aluminium hydride), of which sodium borohydride is preferred.

The amount of the reducing agent (III) is not specifically limited and is generally from 5 to 30 equivalents, preferably from 8 to 25 equivalents, and more preferably from 10 to 20 equivalents to cyanocobalamin (I) or hydroxocobalamin (II).

One of features of the present invention is that methylcobalamin having a high purity equivalent to or higher than products purified by column chromatography can be conveniently obtained in a high yield in the production of methylcobalamin (V) using cyanocobalamin (I) or hydroxocobalamin (II), by sequentially performing a reduction process and a subsequent methylation process stepwise in this order, where necessary precipitating a reaction product hardly soluble in water as crystals or precipitates, and separating and treating the resulting substance. In the reduction process, cyanocobalamin (I) or hydroxocobalamin (II) is reduced generally in an aqueous solution or a hydrous organic solvent in the presence of the reducing agent (III). In the methylation process, the water-soluble methylating agent (IV) is added after reduction to thereby methylate the reductant.

The reducing agent and the water-soluble methylating agent are added to the reaction system in different processes, respectively. More specifically, in the reduction process, the reducing agent is added to thereby convert cyanocobalamin (I) or hydroxocobalamin (II) into a reductant completely. After the reduction process, the water-soluble methylating agent is added to the reaction system to thereby yield methylcobalamin.

Another significant feature of the present invention is that the formation of dimethyl sulfide can be inhibited by sequentially performing the reduction process and the subsequent methylation process stepwise in this order when trimethylsulfoxonium iodide, trimethylsulfoxonium bromide and/or trimethylsulfoxonium chloride among the trimethylsulfur derivatives is used as the water-soluble methylating agent. In the reduction process, cyanocobalamin (I) or hydroxocobalamin (II) is reduced generally in an aqueous solution or a hydrous organic solvent in the presence of the reducing agent (III). In the methylation process, the water-soluble methylating agent (IV) is added after reduction to thereby methylate the reductant.

Dimethyl sulfide is a malodorous harmful substance and adversely affects factory workers and surroundings. Therefore, its emission is severely controlled according to the Offensive Odor Control Law.

When the trimethylsulfur derivative serving as the water-soluble methylating agent coexists with the reducing agent in the reaction system, the trimethylsulfur derivative is reduced and thereby yields dimethyl sulfide that impart burdens on the atmospheric environment. According to the present invention, initially, cyanocobalamin (I) or hydroxocobalamin (II) is reduced with the reducing agent and is converted into a reductant. After the completion of this process, trimethylsulfoxonium iodide, trimethylsulfoxonium bromide and/or trimethylsulfoxonium chloride among the trimethylsulfur derivatives serving as the water-soluble methylating agent is added to thereby methylate the reductant. Thus, excess reduction can be prevented and the formation of dimethyl sulfide can be substantially completely inhibited.

When trimethylsulfonium iodide, trimethylsulfonium bromide and/or trimethylsulfonium chloride is used as the water-soluble methylating agent, dimethyl sulfide forms but its amount is less than that in a "process for producing methylcobalamin in which the methylating agent and the reducing agent coexist in the reaction system" by sequentially performing the reduction process, wherein cyanocobalamin (I) or hydroxocobalamin (II) is reduced generally in an aqueous solution or a hydrous organic solvent in the presence of the reducing agent (III), and the subsequent methylation process, wherein the water-soluble methylating agent (IV) is added to a reductant after reduction to thereby methylate the reductant, stepwise in this order. When the methylating agent and the reducing agent coexist in the reaction system, the methylating agent must be added in excess amount for stabilizing the reaction and thereby yields dimethyl sulfide in an amount corresponding to the excess methylating agent. In contrast, "by separately sequentially performing the reduction process and the subsequent methylation process" according to the present invention, dimethyl sulfide derived from the excess methylating agent is not formed, thus the amount of formed dimethyl sulfide decreases.

Generally, dimethyl sulfide formed in a reaction process is often trapped and removed by 1) an oxidizing agent such as an aqueous solution of a hypochlorite or 2) an organic solvent such as an aqueous solution of dimethylformamide. However, the technique 1) is an oxidation reaction using the oxidizing agent and requires complicated control of complex actions when other components such as hydrogen and hydrogen cyanide in exhausted gas are coexistent. It further requires complicated installation and management of facilities for trapping of the exhaust gas. The technique 2) invites an increased amount of wasted liquid of the organic solvent, thus inviting environmental problems and increased cost caused by the treatment of the waste liquid.

In contrast, the process for producing methylcobalamin and the method for inhibiting the formation of dimethyl sulfide according to the present invention control the formation of dimethyl sulfide itself, do not require additional extra facilities and treatments and are very convenient and useful methods.

The production method according to the present invention enables the production of highly pure methylcobalamin in a high yield using no metal ion or using only a small amount thereof as a cyanide ion scavenger, and the method exhibits an extremely excellent effect in view that no problem arises at removal of metal ion products, which is difficult to filter, from the system.

When methyl iodide is used as a methylating agent, ferrous sulfate is generally often used as a cyanide ion scavenger in combination with methyl iodide. The amount of ferrous sulfate in this case must be 30% by weight or more relative to cyanocobalamin (I) or hydroxocobalamin (II).

However, the present invention enables the production of highly pure methylcobalamin in a high yields because methylation proceeds even when no ferrous sulfate is used as a cyanide ion scavenger.

When a small amount of ferrous sulfate is used as a cyanide ion scavenger, the reaction proceeds at a higher rate, and highly pure methylcobalamin can be obtained in a high yield even by the same aftertreatment procedure as in the case where no ferrous sulfate is used. Likewise, by using a small amount of cobalt chloride, the methylation reaction proceeds with high selectivity to thereby inhibit the formation of impurities, and highly pure methylcobalamin can also be obtained in a high yield.

Examples of the cyanide ion scavenger for use in the present invention, metals or metal salts such as ferrous sulfate, iron powder, Mohr's salt, ferrous chloride, cobalt chloride, nickel chloride or zinc chloride may be proposed. Among them, ferrous sulfate and/or cobalt chloride is particularly preferred. Each of these metals and metal salts can be used alone or in combination.

The amount of the cyanide ion scavenger can be small and is generally from 1 to 30% by weight and preferably from 1 to 10% by weight relative to cyanocobalamin (I) or hydroxocobalamin (II).

The use of a reaction solvent is not specifically limited, and the reaction solvent, if used, is not specifically limited as long as it is inert to cyanocobalamin (I), hydroxocobalamin (II), trimethylsulfur derivative (VI) and methylcobalamin (V). The reaction solvent is generally an aqueous solution or a hydrous organic solvent. The organic solvent is preferably one soluble in water, lower alcohols such as methanol, ethanol, propanol, isopropanol, butanol, isobutanol, sec-butanol or t-butanol; esters such as methyl formate, ethyl formate, methyl acetate, ethyl acetate or isopropyl acetate; ketones such as acetone, 2-butanone or 3-methyl-2-butanone; cyclic ethers such as THF or dioxane; as well as acetonitrile, DMF, DMSO, pyridine, and mixtures of these organic solvents.

The reaction temperature in the reduction process and the methylation process in the present invention is not specifically limited and is generally from 0° C. to 90° C., preferably from 10° C. to 70° C., and more preferably from 15° C. to 50° C.

The reactions in the reduction process and the methylation process in the present invention are preferably performed under flow of an inert gas such as nitrogen gas and/or in the dark (under red light). However, the reaction procedures are not limited thereto.

The present invention can provide an industrially excellent process for producing methylcobalamin. It can also provide a novel industrially excellent process for producing methylcobalamin, which method does not invite the formation of a malodorous harmful substance and is ecological, and a process for inhibiting the formation of a malodorous harmful substance in a production process of methylcobalamin (V). Examples of the advantages of the present invention will be described below. Inhibitory effect of present invention on formation of malodorous harmful substance The method of the present invention comprises performing reactions of a reduction process and of a subsequent methylation process stepwise in this order.

In Examples 1 to 3 (methylating agent: trimethylsulfoxonium bromide) according to the present invention, the concentration of dimethyl sulfide in a reaction pot was measured in the following manner every hour from immediately after the completion of the dropwise addition of an aqueous solution of sodium borohydride. Specifically, dimethyl sulfide was introduced from the reaction pot via a glass tube to a 50% DMF aqueous solution as an absorbent, was subjected to gas absorption by gas-liquid bubbling, and the concentration of collected dimethyl sulfide in the absorbent was determined by capillary gas chromatography. (Capillary gas chromatography was performed using GC HP 6890 manufactured by Agilent, and a DB-624 column. After retaining at 50° C. for 10 minutes, the temperature was elevated to 200° C. at a rate of 15° C. per minute. The gas absorption temperature was 100° C., the detection temperature was 215° C., and the injection amount was 1 µl. At the same time, a sensory test of odor was performed.

As a control experiment, the same procedure was repeated every hour from immediately after the completion of dropwise addition of an aqueous solution of sodium borohydride in the following "process for producing methylcobalamin in which a trimethylsulfur derivative as a water-soluble methylating agent coexists with a reducing agent in the reaction system".

Control Experiment

To 260 ml of ion-exchanged water were added 20 g of cyanocobalamin, 7.66 g of trimethylsulfoxonium bromide, 1.4 g of cobalt chloride hexahydrate, and 15 ml of 2-butanone. After replacing the atmosphere of the system with nitrogen gas, the mixture was heated in a water bath, to which an aqueous solution of sodium borohydride (8 g/40 ml) was added dropwise at the inner temperature of 40° C. over 90 minutes under stirring. After stirring for further 3 hours as it was, the mixture was stirred at a bath temperature of 15° C. overnight. The resulting precipitates were collected by filtration and dried, to give a crude product of the title compound. To the crude product was added a 50% acetone aqueous solution, the mixture was heated at 35° C., was adjusted to pH 7.0 with concentrated hydrochloric acid, followed by dropwise addition of acetone and stirring overnight. The precipitated crystals were collected by filtration and were dried.

The concentrations of formed dimethyl sulfide in each Example are shown in Table 1.

TABLE 1

| the intervals after the dropwise addition of sodium borohydride | immediately after the dropwise addition | 1 hour | 2 hour | 5 hour |
|---|---|---|---|---|
| Example 1 | 0 ppm odorless | 0 ppm odorless | 0 ppm odorless | 0 ppm odorless |
| Example 2 | 0 ppm odorless | 0 ppm odorless | 0 ppm odorless | 0 ppm odorless |
| Example 3 | 0 ppm odorless | 0 ppm odorless | 0 ppm odorless | 0 ppm odorless |
| Control Example 1 | 62.4 ppm malodorous | 1250 ppm malodorous | 697 ppm malodorous | | the upper line: concentration of dimethyl sulfide
the lower line: result of the sensory test of odor In Examples 1 to 3 (methylating agent: trimethylsulfoxonium bromide), no malodor was perceived in the sensory test and no dimethyl sulfide was detected in gas chromatography 1 hr, 2 hr, 3 hr, and 5 hr after the addition of sodium borohydride. In contrast, in the control example in which the water-soluble methylating agent and the reducing agent were in coexistence, malodor was perceived, and dimethyl sulfide in a high concentration was detected at least 3 hr after the addition.

These results show that the production method of methylcobalamin according to the present invention, especially the production method "in which cyanocobalamin (I) or hydroxocobalamin (II) is reduced in the presence of the reducing agent (III), and trimethylsulfoxonium iodide, trimethylsulfoxonium bromide and/or trimethylsulfoxonium chloride is added after reduction to thereby methylate the reductant", does not invite and can effectively inhibit the formation of a malodorous harmful substance.

EXAMPLES

The present invention will be illustrated in further detail with reference to Examples below, which are not intended to limit the scope of the invention.

Example 1

Synthesis of Methylcobalamin

All the procedures in the present example were performed in the dark (under red light).

To 65 ml of ion-exchanged water were added 5 g of cyanocobalamin, 0.35 g of cobalt chloride hexahydrate, and 3.75 ml of 2-butanone. After replacing the inside atmosphere of the system with nitrogen gas, the mixture was heated in a water bath, to which an aqueous solution of sodium borohydride (2 g/10 ml) was added dropwise under stirring at a bath temperature of 38° C. over 60 minutes. After stirring for further 30 minutes as it was, an aqueous solution of trimethylsulfoxonium bromide (1.9 g/10 ml) was further added thereto over 30 minutes. The mixture was stirred for further 3 hours as it was, followed by stirring overnight at a bath temperature of 15° C. The resulting precipitates were collected by filtration and dried to give a crude product of the title compound. To the crude product was added a 50% acetone aqueous solution. After heating at 35° C., the mixture was adjusted to pH 7.0 with concentrated hydrochloric acid. Then, acetone was added dropwise thereinto and the mixture was stirred overnight. The precipitated crystals were collected by filtration and dried, to give the title compound in a yield of 85%. Physical properties of the resulting methylcobalamin:

In a hydrochloric acid buffer (pH 2.0), UVmax was detected at 264–266, 303–307 and 459–462 nm.
In a phosphate buffer (pH 7.0), UVmax was detected at 266–269, 341–344 and 520–524 nm.
Referential values of UVmax (Merck Index, 12th edition)
(0.1 N—HCl): 264, 304 and 462 nm
(pH 7): 266, 342 and 522 nm Example 2

Synthesis of Methylcobalamin

All the procedures in the present example were performed in the dark (under red light).

To 260 ml of ion-exchanged water were added 20 g of cyanocobalamin, 1.4 g of cobalt chloride hexahydrate, and 15 ml of 2-butanone. After replacing the inside atmosphere of the system with nitrogen gas, the mixture was heated in a water bath, to which an aqueous solution of sodium borohydride (8 g/40 ml) was added dropwise under stirring at the internal temperature of 40° C. over 70 minutes. After stirring for further 30 minutes as it was, an aqueous solution of trimethylsulfoxonium bromide (7.66 g/40 ml) was further added thereto over 30 minutes. The mixture was stirred for further 3 hours as it was, followed by stirring overnight at a bath temperature of 15° C. The resulting precipitates were collected by filtration and dried to give a crude product of the title compound. To the crude product was added a 50% acetone aqueous solution. After heating at 35° C., the mixture was adjusted to pH 7.0 with concentrated hydrochloric acid. Then, acetone was added dropwise thereinto and the mixture was stirred overnight. The precipitated crystals were collected by filtration and dried, to give the title compound in a yield of 85%.

Example 3

Synthesis of Methylcobalamin

All the procedures in the present example were performed in the dark (under red light).

To 390 ml of ion-exchanged water were added 30 g of cyanocobalamin, 2.1 g of cobalt chloride hexahydrate, and 22.5 ml of 2-butanone. After replacing the inside atmosphere of the system with nitrogen gas, the mixture was heated in a water bath, to which an aqueous solution of sodium borohydride (12 g/60 ml) was added dropwise under stirring at the internal temperature of 40° C. over 2 hours. After stirring for further 30 minutes as it was, an aqueous solution of trimethylsulfoxonium bromide (11.5 g/60 ml) was further added thereto over 30 minutes. The mixture was stirred for further 3 hours as it was, followed by stirring overnight at a bath temperature of 15° C. The resulting precipitates were collected by filtration and dried to give a crude product of the title compound. To the crude product was added a 50% acetone aqueous solution. After heating at 35° C., the mixture was adjusted to pH 7.0 with concentrated hydrochloric acid. Then, acetone was added dropwise thereinto and the mixture was stirred overnight. The precipitated crystals were collected by filtration and dried, to give the title compound in a yield of 88%.

Example 4

Synthesis of Methylcobalamin

All the procedures in the present example were performed in the dark (under red light).

To 390 ml of ion-exchanged water were added 30 g of cyanocobalamin, 2.1 g of cobalt chloride hexahydrate, and 22.5 ml of 2-butanone. After replacing the inside atmosphere of the system with nitrogen gas, the mixture was heated in a water bath, to which an aqueous solution of sodium borohydride (12 g/60 ml) was added dropwise under stirring at the internal temperature of 40° C. over 2 hours. After stirring for further 30 minutes as it was, an aqueous solution of trimethylsulfoxonium bromide (11.5 g/60 ml) was further added thereto over 30 minutes. The mixture was stirred for further 3 hours as it was, followed by stirring overnight at a bath temperature of 15° C. The resulting precipitates were collected by filtration and dried to give a crude product of the title compound. To the crude product was added a 50% acetone aqueous solution. After heating at 35° C., the mixture was adjusted to pH 7.0 with concentrated hydrochloric acid. Then, acetone was added dropwise thereinto and the mixture was stirred overnight. The precipitated crystals were collected by filtration and dried, to give the title compound in a yield of 87%.

Example 5

Synthesis of Methylcobalamin

All the procedures in the present example were performed in the dark (under red light).

To 390 ml of ion-exchanged water were added 30 g of cyanocobalamin, 2.1 g of cobalt chloride hexahydrate, and 22.5 ml of 2-butanone. After replacing the inside atmosphere of the system with nitrogen gas, the mixture was heated in a water bath, to which an aqueous solution of sodium borohydride (12 g/60 ml) was added dropwise under stirring at the internal temperature of 50° C. over 2 hours. After stirring for further 30 minutes as it was, an aqueous solution of trimethylsulfoxonium bromide (11.5 g/60 ml) was further added thereto over 30 minutes. The mixture was stirred for further 3 hours as it was, followed by stirring overnight at a bath temperature of 15° C. The resulting precipitates were collected by filtration and dried to give a crude product of the title compound. To the crude product was added a 50% acetone aqueous solution. After heating at 35° C., the mixture was adjusted to pH 7.0 with concentrated hydrochloric acid. Then, acetone was added dropwise thereinto and the mixture was stirred overnight. The precipitated crystals were collected by filtration and dried, to give the title compound in a yield of 88%.

Example 6

Synthesis of Methylcobalamin

All the procedures in the present example were performed in the dark (under red light).

To 390 ml of ion-exchanged water were added 30 g of cyanocobalamin, 2.1 g of cobalt chloride hexahydrate, and 22.5 ml of 2-butanone. After replacing the inside atmosphere of the system with nitrogen gas, the mixture was heated in a water bath, to which an aqueous solution of sodium borohydride (12 g/60 ml) was added dropwise under stirring at the internal temperature of 50° C. over 2 hours. After stirring for further 30 minutes as it was, an aqueous solution of trimethylsulfoxonium bromide (11.5 g/60 ml) was further added thereto over 30 minutes. The mixture was stirred for further 3 hours as it was, followed by stirring overnight at a bath temperature of 15° C. The resulting precipitates were collected by filtration and dried to give a crude product of the title compound. To the crude product was added a 50% acetone aqueous solution. After heating at 35° C., the mixture was adjusted to pH 7.0 with concentrated hydrochloric acid. Then, acetone was added dropwise thereinto and the mixture was stirred overnight. The precipitated crystals were collected by filtration and dried, to give the title compound in a yield of 87%.

Example 7

Synthesis of Methylcobalamin

All the procedures in the present example were performed in the dark (under red light).

To 390 ml of ion-exchanged water were added 3 0 g of cyanocobalamin, 2.1 g of cobalt chloride hexahydrate, and 22.5 ml of 2-butanone. After replacing the inside atmosphere of the system with nitrogen gas, the mixture was heated in a water bath, to which an aqueous solution of sodium borohydride (12 g/60 ml) was added dropwise under stirring at the internal temperature of 30° C. over 2 hours. After stirring for further 30 minutes as it was, an aqueous solution of trimethylsulfoxonium bromide (11.5 g/60 ml) was further added thereto over 30 minutes. The mixture was stirred for further 3 hours as it was, followed by stirring overnight at a bath temperature of 15° C. The resulting precipitates were collected by filtration and dried to give a crude product of the title compound. To the crude product was added a 50% acetone aqueous solution. After heating at 35° C., the mixture was adjusted to pH 7.0 with concentrated hydrochloric acid. Then, acetone was added dropwise thereinto and the mixture was stirred overnight. The precipitated crystals were collected by filtration and dried, to give the title compound in a yield of 85%.

Example 8

Synthesis of Methylcobalamin

All the procedures in the present example were performed in the dark (under red light).

To 390 ml of ion-exchanged water were added 3 0 g of cyanocobalamin, 2.1 g of cobalt chloride hexahydrate, and 22.5 ml of 2-butanone. While blowing nitrogen gas at the flow rate of 15 ml/min. in to the system, the mixture was heated in a water bath, to which an aqueous solution of sodium borohydride (12 g/60 ml) was added dropwise under stirring at the internal temperature of 30° C. over 2 hours. After stirring for further 30 minutes as it was, an aqueous solution of trimethylsulfoxonium bromide (11.5 g/60 ml) was further added thereto over 30 minutes. The mixture was stirred for further 3 hours as it was, followed by stirring overnight at a bath temperature of 15° C. The resulting precipitates were collected by filtration and dried to give a crude product of the title compound. To the crude product was added a 50% acetone aqueous solution. After heating at 35° C., the mixture was adjusted to pH 7.0 with concentrated hydrochloric acid. Then, acetone was added dropwise thereinto and the mixture was stirred overnight. The precipitated crystals were collected by filtration and dried, to give the title compound in a yield of 86%.

Example 9

Synthesis of Methylcobalamin

All the procedures in the present example were performed in the dark (under red light).

To 13 L of ion-exchanged water were added 1 Kg of cyanocobalamin, 70 g of cobalt chloride hexahydrate, and 750 ml of 2-butanone. After replacing the inside atmosphere of the system with nitrogen gas, the mixture was heated in a water bath, to which an aqueous solution of sodium borohydride (400 g/2 L) was added dropwise while keeping and stirring at the internal temperature of 35° C.±5° C. over 120 minutes. An aqueous solution of trimethylsulfoxonium bromide (383 g/2 L) was further added thereto over 30 minutes. The mixture was stirred for further 3 hours as it was, followed by stirring overnight at a bath temperature of 15° C. The resulting precipitates were collected by filtration and dried to give a crude product of the title compound. To the crude product was added a 50% acetone aqueous solution. After heating at 35° C., the mixture was adjusted to pH 7.0 with concentrated hydrochloric acid. Then, acetone was added dropwise thereinto and the mixture was stirred overnight. The precipitated crystals were collected by filtration and dried, to give the title compound in a yield of 87%.

The invention claimed is:

1. A two-step process for producing methylcobalamin (V), comprising the sequential steps of A) and B):
   A) reducing cyanocobalamin (I) or hydroxocobalamin (II) represented by the following formula in the presence of a reducing agent (III) that is sodium borohydride, and
   B) methylating the reductant by adding a water-soluble methylating agent (IV)

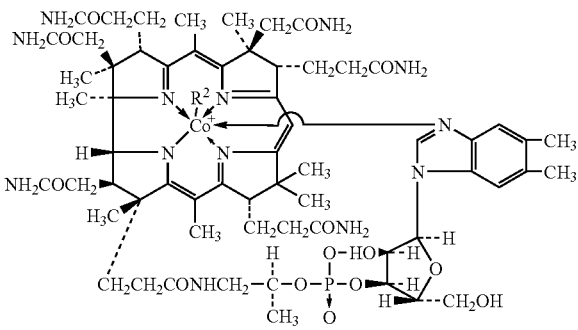

$R^2$=CN: Cyanocobalamin (I)
$R^2$=OH: Hydroxocobalamin (II)
$R^2$=CH: Methylcobalamin (V)

wherein the water-soluble methylating agent (IV) is a trimethylsulfur derivative (VI) represented by the following formula:

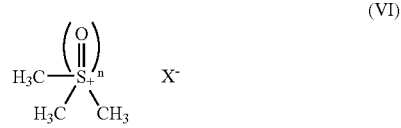

(VI)

wherein X is a halogen atom or a methoxysulfonyloxy group, and n is 0 or 1; and wherein the amount of the trimethylsulfur derivative (VI) added is from 1.0 to 5.0 equivalents to cyanocobalamin (I) or hydroxocobalamin (II).

2. A two-step process for producing methylcobalamin (V), comprising the sequential steps of A) and B):
A) reducing cyanocobalamin (I) or hydroxocobalamin (II) in an aqueous solution or a hydrous organic solvent in the presence of a reducing agent (III) that is sodium borohydride; and
B) methylating the reductant by adding a trimethylsulfur derivative (VI) represented by the following formula:

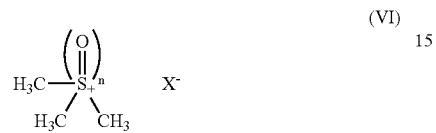

(VI)

wherein X is a halogen atom or a methoxysulfonyloxy group, and n is 0 or 1; and
wherein the amount of the trimethylsulfur derivative (VI) added is from 1.0 to 5.0 equivalents to cyanocobalamin (I) or hydroxocobalamin (II).

3. A multi-step process for producing methylcobalamin (V), comprising the sequential steps of A) to C):
A) reducing cyanocobalamin (I) or hydroxocobalamin (II) in an aqueous solution or a hydrous organic solvent in the presence of a reducing agent (III) that is sodium borohydride;
B) methylating the reductant by adding a trimethylsulfur derivative (VI) represented by the following formula:

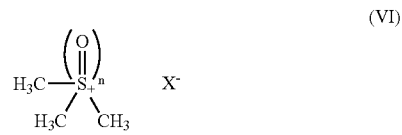

(VI)

wherein X is a halogen atom or a methoxysulfonyloxy group, and n is 0 or 1; and

C) precipitating the reaction product as crystals or precipitates; and
wherein the amount of the trimethylsulfur derivative (VI) added is from 1.0 to 5.0 equivalents to cyanocobalamin (I) or hydroxocobalamin (II).

4. A multi-step process for producing methylcobalamin (V)1 comprising the sequential steps of A) to C):
A) reducing cyanocobalamin (I) or hydroxocobalamin (II) in an aqueous solution or a hydrous organic solvent in the presence of a cyanide ion scavenger and a reducing agent (III) that is sodium borohydride;
B) methylating the reductant by adding a trimethylsulfur derivative (VI) represented by the following formula:

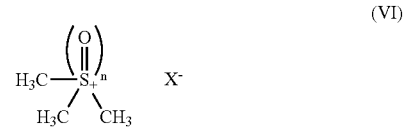

(VI)

wherein X is a halogen atom or a methoxysulfonyloxy group, and n is 0 or 1; and
C) precipitating the reaction product as crystals or precipitates; and
wherein the amount of the trimethylsulfur derivative (VI) added is from 1.0 to 5.0 equivalents to cyanocobalamin (I) or hydroxocobalamin (II).

5. The process for producing methylcobalamin (V) according to claim 1, 2, 3 or 4, wherein the trimethylsulfur derivative (VI) is trimethylsulfoxonium iodide, trimethylsulfonium iodide, trimethylsulfoxonium bromide, trimethylsulfonium bromide, trimethylsulfoxonium chloride and/or trimethylsulfonium chloride.

6. The process for producing methylcobalarnin (V) according to claim 4, wherein the cyanide ion scavenger is ferrous sulfate and/or cobalt chloride.

7. The process for producing methylcobalamin (V) according to claim 4 or 6, wherein the amount of the cyanide ion scavenger is from 1 to 30% by weight relative to cyanocobalamin (I) or hydroxocobalamin (II).

* * * * *

UNITED STATES PATENT AND TRADEMARK OFFICE
CERTIFICATE OF CORRECTION

| | |
|---|---|
| PATENT NO. | : 7,220,855 B2 |
| APPLICATION NO. | : 10/476381 |
| DATED | : May 22, 2007 |
| INVENTOR(S) | : Yoshihiko Hisatake et al. |

It is certified that error appears in the above-identified patent and that said Letters Patent is hereby corrected as shown below:

Title page, item [30] Foreign Application Priority Data:

"June 5, 2002" should read --June 5, 2001--

In Column 14, line 7:

"(V) 1" should read --(V)--

Signed and Sealed this

Sixteenth Day of October, 2007

JON W. DUDAS
*Director of the United States Patent and Trademark Office*